United States Patent [19]

Paradis et al.

[11] Patent Number: 4,615,693
[45] Date of Patent: Oct. 7, 1986

[54] ADMINISTRATION OF FLUIDS

[75] Inventors: Joseph R. Paradis, Holden; Eugene J. Zurlo, Concord, both of Mass.

[73] Assignee: Nypro Inc., Clinton, Mass.

[21] Appl. No.: 593,970

[22] Filed: Mar. 27, 1984

[51] Int. Cl.⁴ .............................................. A61M 5/00
[52] U.S. Cl. .................................. 604/122; 604/323; 604/325; 604/251
[58] Field of Search ....................... 604/122, 251–255, 604/9, 30, 34, 237, 323, 325, 335; 137/843

[56] References Cited

U.S. PATENT DOCUMENTS

| | | | |
|---|---|---|---|
| 2,999,499 | 6/1958 | Willet | 604/251 |
| 3,021,841 | 2/1962 | Burke | 604/252 |
| 3,311,268 | 11/1964 | Fields | 604/122 |
| 3,620,500 | 2/1970 | Santomieri | 604/246 |
| 3,796,245 | 3/1974 | Wildensteiner | 604/255 |
| 3,807,445 | 4/1974 | McPhee | 137/843 |
| 4,158,362 | 6/1979 | Durrett et al. | 604/251 |
| 4,395,260 | 7/1983 | Todd et al. | 604/122 |

Primary Examiner—Dalton L. Truluck
Assistant Examiner—Karen L. Kaechele
Attorney, Agent, or Firm—George E. Kersey

[57] ABSTRACT

A drip chamber apparatus wherein the base of the drip chamber includes an apertured disk with a series of concentric stepped recesses against which is positioned a valve diaphragm. There is provided a pre-biasing member which applies pressure to the valve diaphragm to maintain the valve seated in a closed position. The pre-biasing member is axially adjustable to vary the pre-biasing pressure.

11 Claims, 5 Drawing Figures

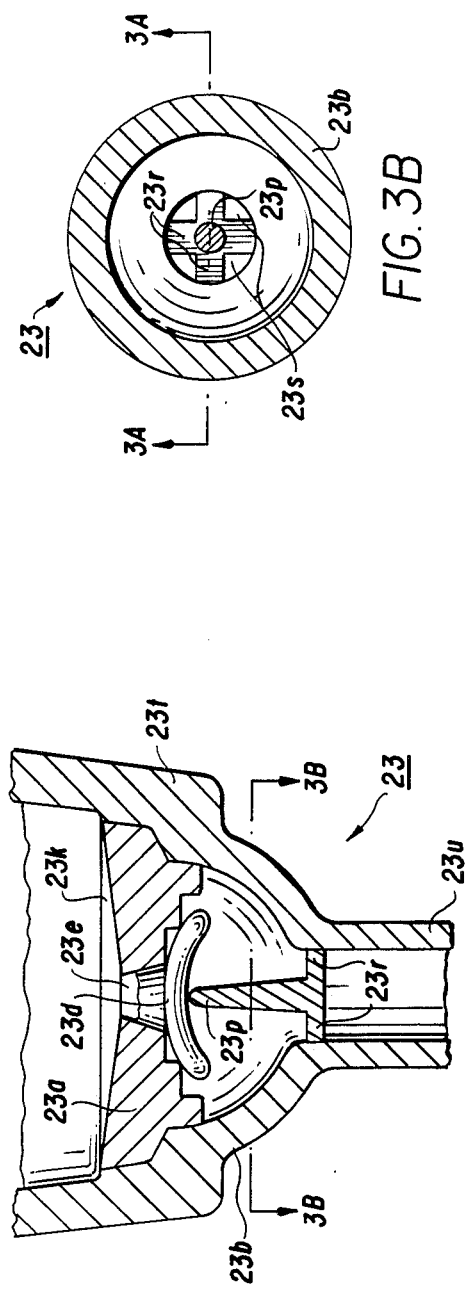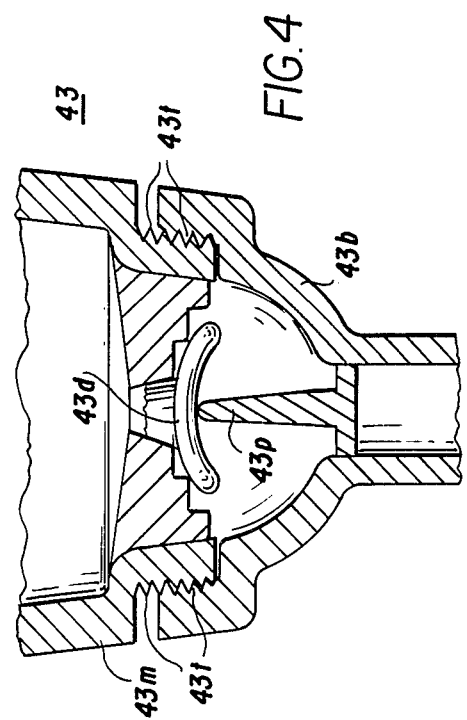

ADMINISTRATION OF FLUIDS

BACKGROUND OF THE INVENTION

This invention relates to the administration of fluids to patients, and more particularly, to the intravenous administration of fluids using drip chambers.

In the administration of fluids, such as plasma and glucose solutions, it is customary practice to administer the solution through a transparent drip chamber in order to permit control over the rate at which the solution is administered. The drip chamber is connected at its input end to the source of the solution being administered, and is further connected at its output end to the patient by a flexible tube which includes a regulating clamp or similar control device. Depending on the setting of the regulating clamp, the amount of solution entering the chamber increases or decreases. In the general case the entering solution is in the form of droplets and the frequency of the droplets gives an indication of the rate of solution administration.

As long as there is a continuous flow of solution from the source through the drip chamber to the patient, there is no danger to the patient. However, when the fluid of the source becomes exhausted, or when the source which has been depleted is being substituted by a fresh source of supply, there is the danger that air will enter the patient through the flexible tubing connected to the drip chamber.

According, it is an object of the invention to facilitate the administration of fluids to patients, particularly in the case of intravenous application.

Another object of the invention is to adapt the drip chamber for the protection of the patient, without sacrificing the advantages provided by the existence of the drip chamber.

Still another object of the invention is to adapt a drip chamber for the protection of the patient without undo complexity and cost in the administrative system.

SUMMARY OF THE INVENTION

In accomplishing the foregoing and related objects, the invention provides for the modification of the conventional drip chamber used in the administration of fluids by providing a flexible diaphragm at the outlet of the chamber before the position of connection of the flexible feed tube that extends to the patient.

In accordance with one aspect of the invention, the base of the drip chamber includes an apertured disk that is press-fit into the chamber above its outlet.

In accordance with another aspect of the invention, the apertured disk of the chamber includes a set of stepped concentric recesses that face the outlet of the chamber. The diaphragm is positioned against the stepped recesses, and the existence of the stepping assures the desired seal between the apertured disk and the diaphragm. As long as the diaphragm is seated against the stepping of the apertued disk, there can be no flow from the chamber into the flexible tubing that extends to the patient. When a source of fluid is positioned for feed into the chamber, the pressure of the droplets which are funneled to the diaphragm by a conical depression on the apertured disk exert pressure on the diaphragm to cause it to open and pass the fluid droplets.

In accordance with a further aspect of the invention, the diaphragm is prebiased against the stepping of the apertured disk to cause the accumulation of a residual amount of fluid in the aperture of the disk above the diaphragm. This reservoir assures an airtight seal at the diaphragm and prevents the entry of air or other gas into the patient when the source of fluid is exhausted, or during the changeover operation that takes place when a spent source is replaced by a fresh source.

In accordance with yet another aspect of the invention, the prebiasing of the diaphragm against the stepping of the apertured disk takes place using a multiplicity of prongs which are positioned circumferentially around the outlet of the chamber with channelling ribs that extend into the outlet to promote the desired flow of the fluid from the chamber into the flexible tube that leads to the patient.

In accordance with still another aspect of the invention, the prebiasing of the diaphragm may be accomplished with a single prong that extends outwardly from an apertured support at the outlet of the chamber.

DESCRIPTION OF THE DRAWING

Other aspects of the invention will become apparent after considering several illustrative embodiments taken in conjunction with the drawings in which:

FIG. 3A is a cross sectional view of an alternative drip chamber in accordance with the invention;

FIG. 3B is a cross sectional view of the modified portion of the drip chamber of FIG. 3A; and FIG. 4 is a partial sectional view of still another modified drip chamber in accordance with the invention.

DETAILED DESCRIPTION

Figure 1:
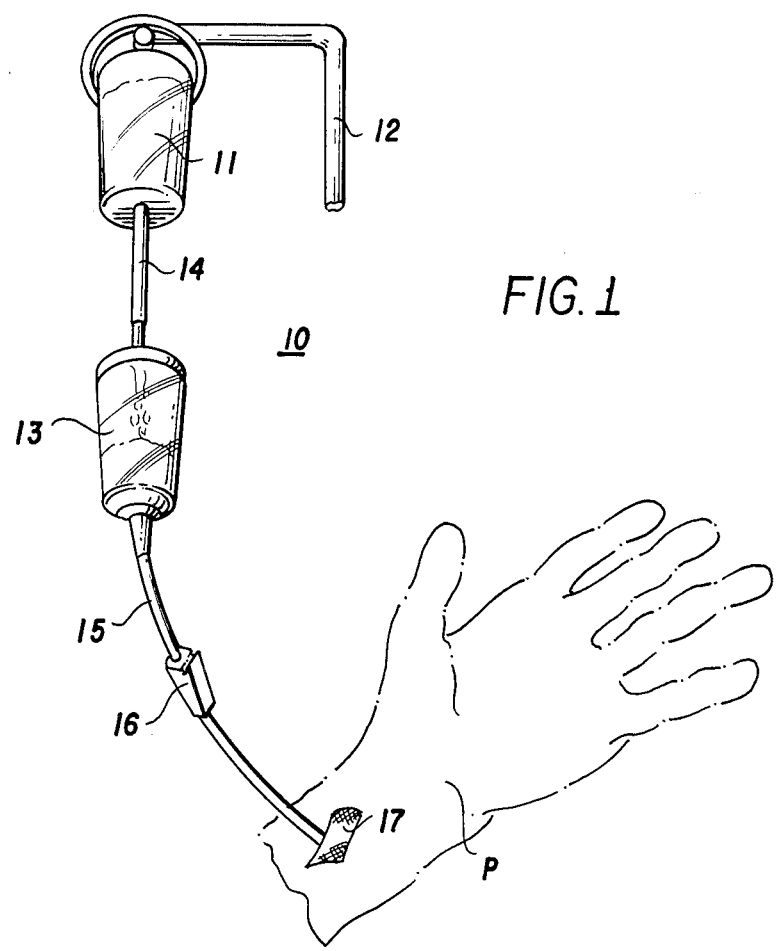
FIG. 1 is a partial perspective view showing the administration of fluids to a patient in accordance with the invention.

With reference to the drawings, FIG. 1 shows a partial system 10 for the flow guarded administration of fluids from a source 11 to a patient P in accordance with the invention. The source 11 is suspended in conventional fashion from a support 12 and contains the fluidic material that is to be administered to the patient P. In order to control the administration from the source 11 a drip chamber 13 is interposed between the source 11 and the patient P. The connection from the source 11 to the chamber 13 is by a customary plastic tube 14 and the connection from the chamber 13 to the patient P is by a further plastic tube 15 which includes a control mechanism 16 such as a positionable roller which can be moved relative to the tubing 15 in order to constrict its opening and thus regulate flow to the patient P. The connection of the tubing 15 to the patient P is made in customary fashion by, for example, a needle which is covered with a bandage 17.

Figure 2:
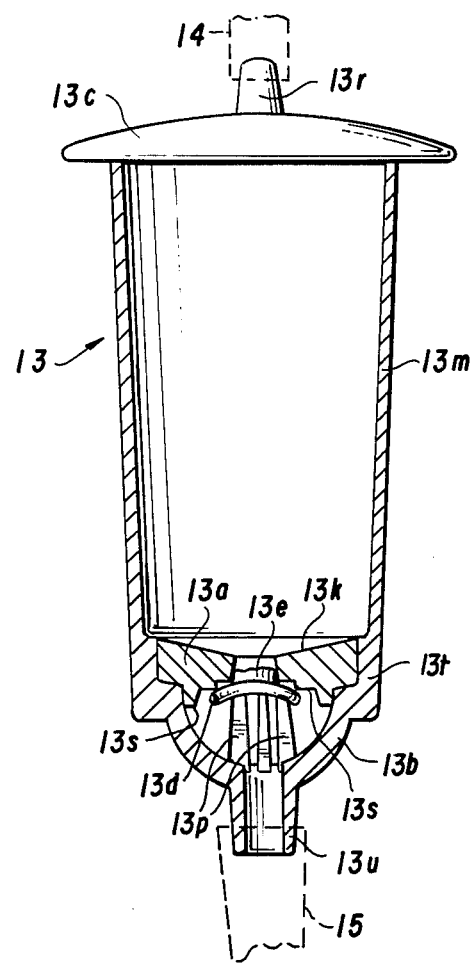
FIG. 2 is a cross sectional view of the drip chamber of FIG. 1 which has been modified in accordance with the invention.

In order to guard against the entry of undesirable gases such as air into the patient P the drip chamber 13 is adapted as shown in the cross sectional view of FIG. 2 by having an outlet 13u with a bowl portion 13b that supports a set of prongs 13p. The latter are used for the prebiasing of a flexible diaphragm 13d which is positioned against stepping 13s of an apertured 13a.

The chamber 13 includes a main body 13m which extends above the apertured disk 13a to a cover 13c which is conventionally penetrated by a piercing pin 13n in order to provide access to the chamber 13 from the source 11 by the tubing 14 of FIG. 1. The portion of the body above the bowl 13b has a thickened wall 13t in order to accommodate the apertured disk 13a by a press-fit.

In addition the apertured disk 13a includes a conical recess 13k to promote the flow of the droplets entering at the cover 13c from the inlet line 14. The central portion of the apertured disk 13a includes a cylindrical channel 13e which accumulates sufficient fluid to provide an airtight seal at the stepping 13s until the pressure of the fluid entering the chamber 13 exceeds a prescribed level, at which point the diaphragm 13d is unseated from the stepping 13s and the fluid flows into the outlet line 15 as guided by ribs 13r of the prongs 13p which extend into the outlet 13u.

A further modification 23 of the chamber 13 of FIG. 1 is shown in partial cross section in FIG. 3A. The diaphragm 23d is positioned against the stepping 23s of the press fit apertured disk 23a by a single prong 23p.

The particular arrangement of the prong 23p relative to the outlet 23u is illustrated in FIG. 3B which shows the prong 23p positioned at the cross point of ribbing 23r. The sectors 23s between adjoining ribs 23r and the main wall of the outlet 23u provide the desired passage for the outward flow of the fluid entering the chamber 23.

A further modification of the invention is shown in FIG. 4 where the chamber 43 includes a removable base 43b that is secured to the main body 43m by threading 43t. The base 43b includes a central prong 43p which applies the desired prebiasing pressure to the diaphragm 43d. The extent of the prebiasing is governed by the extent to which the base 43b is threaded against the main body 43m.

While various aspects of the invention have been set forth by the drawings and specification, it is to be understood that the foregoing detailed description is for illustration only and that various changes in parts, as well as the substitution of equivalent constituents for those shown and described may be made without departing from the spirit and scope of the invention as set forth in the appended claims.

What is claimed is:

1. A flow-guarded drip chamber comprising
   a main housing for receiving fluid droplets in an axial direction;
   an outlet in said main housing for said droplets;
   a support member positioned in said outlet and having a central opening therethrough; said supported member being an apertured disc that is positioned in said housing before said outlet and including a set of a plurality of stepped concentric recesses facing said outlet;
   a flexible disk diaphragm interposed between said support member and said outlet; and
   means associated with said outlet for externally adjusting the pre-biasing pressure of said diaphragm against said support member in said axial direction.

2. Apparatus as defined in claim 1 wherein said main housing is fabricated from flexible translucent material in order to permit the monitoring by visual observation of the droplets entering said housing.

3. Apparatus as defined in claim 1 wherein said diaphragm is positioned against said stepped recesses.

4. Apparatus as defined in claim 3 wherein said diaphragm is positioned against said support member by a longitudinally extending prong which is in alignment with the axis of said outlet.

5. Apparatus as defined in claim 4 wherein said longitudinally extending prong is supported in alignment with the central axis of said outlet by an open grid.

6. Apparatus as defined in claim 3 wherein said diaphragm is positioned against the stepped recesses by a plurality of prongs which are disposed about said outlet.

7. Apparatus as defined in claim 6 wherein each of said prongs has a shoulder which projects into said outlet; thereby to facilitate the flow of said droplets into the outlet channel.

8. Apparatus as defined in claim 6 wherein said prongs limit the extent to which said diaphragm flexes under the flow of said droplets.

9. The method of guarding flow to and from a drip chamber which comprises the steps of:
   (a) introducing fluid droplets into a main housing of said chamber;
   (b) collecting said droplets at the base of said chamber at an exit port which is temporarily sealed by an elastically-expanded diaphragm;
   (c) causing said diaphragm to yield at the peripheries of said exit port when the mass of said droplets exceeds a prescribed threshold; and
   (d) adjusting said threshold of said valve in said axial direction.

10. A method in accordance with claim 9 wherein said diaphragm is separated from the main chamber of said housing by a support member.

11. A method in accordance with claim 10 wherein said support member is adjustable relative to said diaphragm in order to control the threshold level at which the accumulated droplets exit from said chamber.

* * * * *